United States Patent
Kishimoto et al.

(10) Patent No.: US 9,066,682 B2
(45) Date of Patent: Jun. 30, 2015

(54) FUNDUS IMAGING APPARATUS AND FUNDUS IMAGING METHOD

(75) Inventors: Takuya Kishimoto, Tokyo (JP); Sakuya Tamada, Tokyo (JP)

(73) Assignee: Sony Corporation, Tokyo (JP)

(*) Notice: Subject to any disclaimer, the term of this patent is extended or adjusted under 35 U.S.C. 154(b) by 182 days.

(21) Appl. No.: 13/398,547

(22) Filed: Feb. 16, 2012

(65) Prior Publication Data

US 2012/0229769 A1    Sep. 13, 2012

(30) Foreign Application Priority Data

Mar. 10, 2011   (JP) ................ 2011-052709

(51) Int. Cl.
*A61B 3/10*   (2006.01)
*A61B 3/12*   (2006.01)
*A61B 5/00*   (2006.01)

(52) U.S. Cl.
CPC ... *A61B 3/10* (2013.01); *A61B 3/12* (2013.01); *A61B 5/0071* (2013.01); *A61B 3/1015* (2013.01)

(58) Field of Classification Search
CPC ................ A61B 3/10; A61B 5/0071
USPC .......................... 351/210, 221, 246
See application file for complete search history.

(56) References Cited

U.S. PATENT DOCUMENTS

| | | | |
|---|---|---|---|
| 4,838,679 A | 6/1989 | Bille | |
| 5,279,298 A * | 1/1994 | Flower | 600/321 |
| 2004/0165259 A1* | 8/2004 | Mueller et al. | 359/385 |
| 2011/0236310 A1* | 9/2011 | Watanabe et al. | 424/1.69 |

FOREIGN PATENT DOCUMENTS

| | | |
|---|---|---|
| JP | 2004-159955 | 6/2004 |
| JP | 2010-057896 | 3/2010 |

* cited by examiner

*Primary Examiner* — Jordan Schwartz
(74) *Attorney, Agent, or Firm* — K&L Gates LLP

(57) ABSTRACT

Provided is a fundus imaging apparatus including a wavefront adjuster and a detector. The wavefront adjuster is configured to adjust a wavefront of a femtosecond pulsed laser beam incident on an ocular fundus to be examined. The detector is configured to detect fluorescence generated in a multi-photon excitation process by the femtosecond pulsed laser beam incident on the ocular fundus to be examined. The wavefront adjuster is further configured to adjust the wavefront so that an intensity of the fluorescence to be detected by the detector becomes a maximum value.

13 Claims, 1 Drawing Sheet

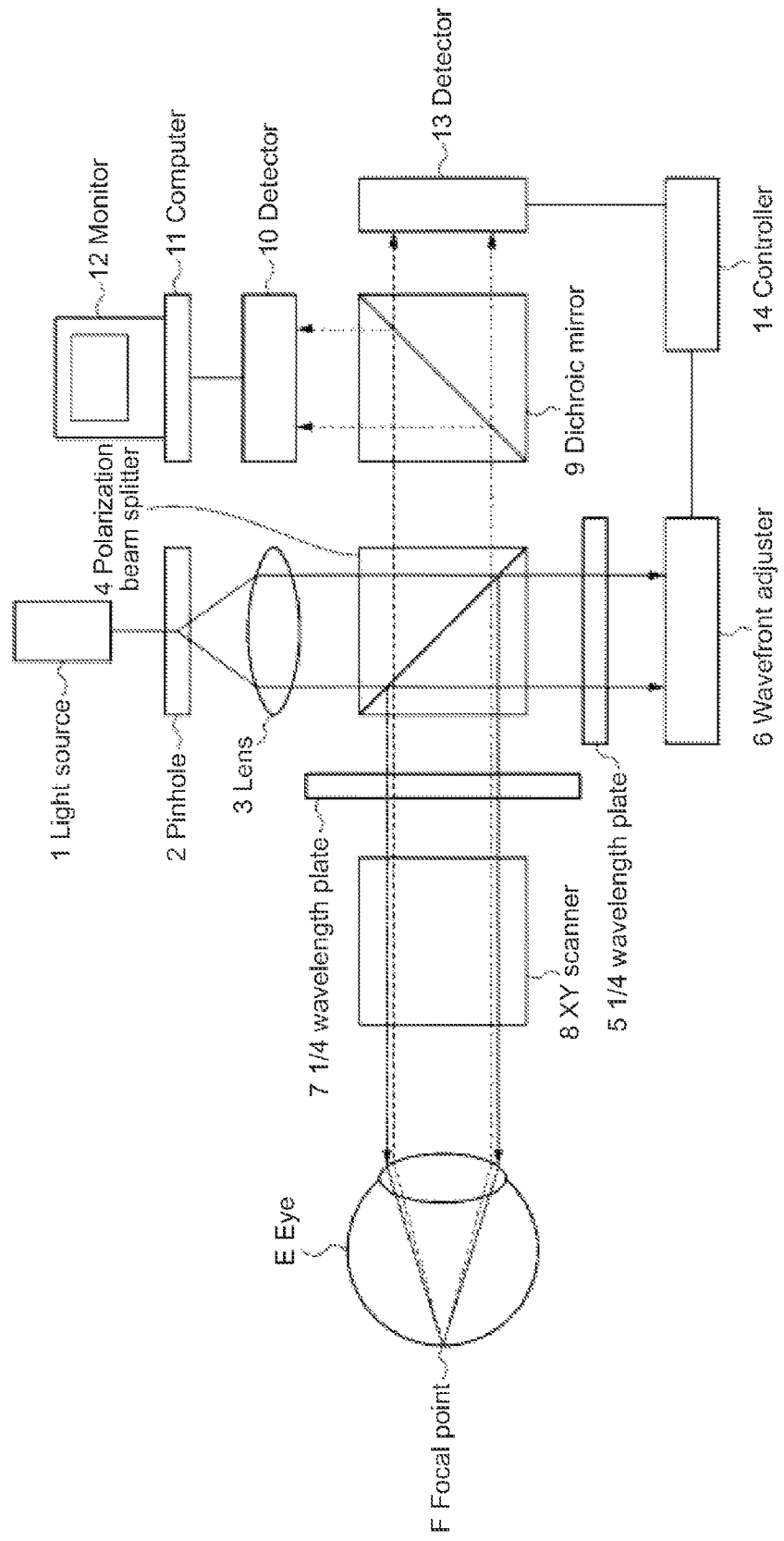

… (1) …

FUNDUS IMAGING APPARATUS AND FUNDUS IMAGING METHOD

CROSS REFERENCES TO RELATED APPLICATIONS

The present application claims priority to Japanese Priority Patent Application JP 2011-052709 filed in the Japan Patent Office on Mar. 10, 2011, the entire content of which is hereby incorporated by reference.

BACKGROUND

The present disclosure relates to a fundus imaging apparatus and a fundus imaging method. More specifically, the present disclosure relates to a fundus imaging apparatus including a mechanism for correcting optical aberration, which occurs due to a cornea, a crystalline lens, etc., and the like.

In order to image an ocular fundus, a laser scanning funduscope has been used (e.g. see Japanese Patent Application Laid-open No. 2004-159955). In the laser scanning funduscope, due to front components (cornea and crystalline lens) of an eye, optical aberration occurs in a laser beam incident on the ocular fundus.

As a technique for correcting such optical aberration, Japanese Patent Application Laid-open No. 2010-57896 discloses an imaging system that compensate for optical aberration by using an optical system including a wavefront sensor.

SUMMARY

There is a need for providing a fundus imaging apparatus capable of compensating for optical aberration due to front components of an eye by optimizing a wavefront shape without using a wavefront sensor.

According to embodiments of the present disclosure, there are provided a fundus imaging apparatus and an optical aberration correcting apparatus, each of which includes a wavefront adjuster and a detector. The wavefront adjuster is configured to adjust a wavefront of a femtosecond pulsed laser beam incident on an ocular fundus to be examined. The detector is configured to detect fluorescence generated in a multi-photon excitation process by the femtosecond pulsed laser beam incident on the ocular fundus to be examined The wavefront adjuster is further configured to adjust the wavefront so that an intensity of the fluorescence to be detected by the detector becomes a maximum value.

In multi-photon excitation by the femtosecond pulsed laser beam, target excitation light is generated only in a focal plate and fluorescence due to the multi-photon excitation process is generated. Therefore, when the intensity of the generated fluorescence becomes maximum, a laser beam is converged to the focal plate at maximum efficiency, that is, at minimum optical aberration. Thus, by adjusting the wavefront of the laser beam so that the intensity of the fluorescence to be detected becomes maximum, the optical aberration can be effectively compensated.

Further, according to embodiments of the present disclosure, there are provided a fundus imaging method and an optical aberration correcting method, each of which includes adjusting a wavefront of a femtosecond pulsed laser beam incident on an ocular fundus to be examined so that an intensity of fluorescence generated in a multi-photon excitation process by the femtosecond pulsed laser beam incident on the ocular fundus to be examined becomes a maximum value.

In this fundus imaging method and the like, the fluorescence may be one of fluorescence generated from a fluorescent dye present in the ocular fundus to be examined and autofluorescence generated from a tissue of the ocular fundus to be examined.

According to the present disclosure, the fundus imaging apparatus capable of compensating for the optical aberration due to the front components of the eye by optimizing the wavefront shape without using the wavefront sensor can be provided.

These and other objects, features and advantages of the present disclosure will become more apparent in light of the following detailed description of best mode embodiments thereof, as illustrated in the accompanying drawing.

Additional features and advantages are described herein, and will be apparent from the following Detailed Description and the figures.

BRIEF DESCRIPTION OF THE FIGURES

FIG. 1 is a schematic view for illustrating a configuration of a fundus imaging apparatus according to an embodiment of the present disclosure.

DETAILED DESCRIPTION

Hereinafter, an embodiment of the present disclosure will be described with reference to the drawing. It should be noted that the embodiment described in the following is one example of typical embodiments of the present disclosure and this is not to be construed as limiting the range of the present disclosure.

FIG. 1 schematically shows a configuration of a fundus imaging apparatus according to an embodiment of the present disclosure. In FIG. 1, the reference numeral 1 denotes a femtosecond pulsed laser light source. For the femtosecond pulsed laser light source 1, for example, a light source having a wavelength of 780 nm, a pulse width of 200 fs or less, an output stability of about ±0.5%, a repeating frequency of 80 MHz, and an average light output of about 2 W is desirably used. From such a light source, a laser beam excellent in accessibility to a deep part can be obtained because it is hardly absorbed and diffused due to water and blood in body tissues. It should be noted that an output wavelength of the femtosecond pulsed laser light source 1 can be appropriately changed within a range of from 650 to 1100 nm depending on a measurement condition.

A laser beam emitted from the femtosecond pulsed laser light source 1 passes through a pinhole 2, a lens 3, a polarization beam splitter 4, and a ¼ wavelength plate 5 and enters a wavefront adjuster 6. Then, the laser beam is reflected by the wavefront adjuster 6, passes through the ¼ wavelength plate 5, the polarization beam splitter 4, a ¼ wavelength plate 7, and an XY scanner 8, and enters an eye E. The laser beam that is emitted from the femtosecond pulsed laser light source 1 and enters the eye E is shown by the continuous arrow in FIG. 1. Further, a focal point of the laser beam incident on the eye E is denoted by the reference symbol f, the focal point being located in an ocular fundus.

The wavefront adjuster 6 functions to change a wavefront of the laser beam incident on the eye E. In the wavefront adjuster 6, a deformable mirror and a liquid crystal element, which have been used in the past. The wavefront adjuster 6 reflects an incident laser beam, applying to it a predetermined wavefront change according to a signal input from a controller 14 to be described next. It should be noted that in the wavefront adjuster 6, not only a reflection type liquid crystal element, but also a transmission type liquid crystal element may be adopted.

When the laser beam incident on the eye E is converged at the focal point f, excitation light is generated in a focal plate and fluorescence is generated in a multi-photon excitation process. The generated fluorescence passes through the XY scanner 8, the ¼ wavelength plate 7, and the polarization beam splitter 4 and is separated by a dichroic mirror 9.

One part of the separated fluorescence is detected by a detector 10, converted into an electrical signal, and output to a computer 11. The computer 11 produces an image according to the electrical signal and displays it on a monitor 12. Due to the XY scanner 8 scanning the incident laser beam, a two-dimensional image of the ocular fundus is displayed on the monitor 12. The detector 10 and a detector 13, to be described next, may be each constituted of, for example, a photo multiplier tube (PMT) or an area imaging element such as a charge coupled device (CCD) and a complementary metal-oxide semiconductor (CMOS).

The other part of the separated fluorescence is detected by the detector 13, converted into an electrical signal, and output to the controller 14. Here, although the example in which the dichroic mirror 9 reflects light having a particular wavelength region to the detector 10 and causes light having other wavelength regions to pass through the detector 13 is shown in the FIG. 1, the dichroic mirror 9 may reflects the light having a particular wavelength region to the detector 13 and causes the light having other wavelength regions to pass through the detector 10.

The controller 14 controls the wavefront adjuster 6 so that the intensity of the fluorescence to be detected by the detector 13 becomes a maximum value. For example, in the case where the detector 13 is constituted of the PMT, the controller 14 controls the wavefront adjuster 6 so that an output signal from the detector 13 becomes a maximum value, to thereby change the wavefront of the laser beam. Further, for example, in the case where the detector 13 is constituted of the area imaging element, the controller 14 controls the wavefront adjuster 6 so that a luminescent spot has a minimum area and its center portion has a maximum luminance, to thereby change the wavefront of the laser beam.

In multi-photon excitation by a femtosecond pulsed laser beam, target excitation light is generated only in the focal plate and fluorescence due to the multi-photon excitation process is generated. Therefore, when the intensity of the generated fluorescence becomes maximum, the laser beam is converged at the focal point f at maximum efficiency. In other words, the laser beam is converged at the focal point f at minimum optical aberration. Thus, by controlling the wavefront adjuster 6 so that the intensity of the fluorescence to be detected by the detector 13 becomes a maximum value, to thereby adjust the wavefront of the laser beam incident on the eye E, the optical aberration can be effectively compensated.

It should be noted that in the controller 14, for example, an apparatus including a general-purpose computer provided with a central processing unit (CPU), a memory, a recording apparatus (hard disk), and the like may be adopted, the computer installing a program for executing the above-mentioned control.

The fluorescence to be detected by the detector 13 may be fluorescence generated from a fluorescent dye present in the ocular fundus to be examined or autofluorescence generated from a tissue of the ocular fundus to be examined.

In the case of using the fluorescent dye, a fluorescent dye such as fluorescein or indocyanine green, which has been used in the past, is administered into a vein of a subject so as to be introduced into a blood vessel in the eye E. Then, the wavefront adjuster 6 is controlled so that the intensity of fluorescence from the fluorescent dye to be detected by the detector 13 becomes a maximum value. In this manner, it is possible to compensate for the optical aberration due to the front components of the eye and converge a laser beam to the blood vessel being the focal point f at high efficiency, which is advantageous especially for imaging tissues including a choroid and a retina.

Further, in the case of detecting the autofluorescence, fluorescence from various autofluorescent substances present in tissues of the ocular fundus is detected. For example, it is known that in a retinal dye epithelial cell (RPE), lipofuscin granules that exhibit high autofluorescence accumulate. Therefore, if the wavefront adjuster 6 is controlled so that the intensity of fluorescence to be detected from the RPE becomes a maximum value, a laser beam can be converged to the RPE at high efficiency, which is advantageous especially for imaging tissues including retinal dye epithelium. In addition to this, as the autofluorescent substances present in the tissues of the ocular fundus, there are exemplified melanin, collagen, hemoglobin, retinal, and derivatives thereof, retinoic acid and a derivative thereof, aromatic amino acid such as tyrosine, tryptophan and a dimer thereof, nicotinamide adenine dinucleotide phosphate (NADPH), riboflavin, folic acid, pyridoxine, a protein having a porphyrin skeleton, cytochrome enzymes such as cytochrome P450, and advanced glycation endproducts. Those autofluorescent substances can be appropriately selected depending on a tissue to be an imaging target.

With the fundus imaging apparatus and the like according to the present disclosure, it is possible to effectively compensate for the optical aberration due to the front components of the eye. Thus, the fundus imaging apparatus and the like according to the present disclosure can obtain a high-accurate ocular fundus image and thus contribute to an improvement in diagnostic accuracy of the examination of the ocular fundus.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A fundus imaging apparatus, comprising:
   a laser light source;
   a wavefront adjuster configured to adjust a wavefront of a femtosecond pulsed laser beam from the laser light source that is incident on an ocular fundus to be examined, at least a portion of the ocular fundus configured to generate fluorescence or autofluorescence in response to a multi-photon excitation process by the femtosecond pulsed laser beam incident on the ocular fundus to be examined;
   an XY scanner configured to scan the incident laser beam and obtain two-dimensional image information of the ocular fundus;
   a detector configured to detect the fluorescence or autofluorescence generated, wherein the wavefront adjuster is further configured to adjust the wavefront so that an intensity of the fluorescence or autofluorescence to be detected by the detector becomes a maximum value; and
   a dichroic mirror configured to separate the generated fluorescence or autofluorescence into at least a first wavelength range and a second wavelength range.

2. An optical aberration correcting apparatus, comprising:
a laser light source;
a wavefront adjuster configured to adjust a wavefront of a femtosecond pulsed laser beam incident on an ocular fundus to be examined, at least a portion of the ocular fundus configured to generate fluorescence or autofluorescence in response a multi-photon excitation process by the femtosecond pulsed laser beam incident on the ocular fundus to be examined;
an XY scanner configured to scan the incident laser beam and obtain two-dimensional image information of the ocular fundus;
a detector configured to detect the fluorescence our autofluorescence generated, wherein the wavefront adjuster is further configured to adjust the wavefront so that an intensity of the fluorescence or autofluorescence to be detected by the detector becomes a maximum value; and
a dichroic mirror configured to separate the generated fluorescence or autofluorescence into at least a first wavelength range and a second wavelength range.

3. A fundus imaging method, comprising:
adjusting a wavefront of a femtosecond pulsed laser beam from a laser light source that is incident on an ocular fundus to be examined so that an intensity of fluorescence or autofluorescence generated in a multi-photon excitation process by the femtosecond pulsed laser beam incident on the ocular fundus to be examined becomes a maximum value, at least a portion of the ocular fundus configured to generate said fluorescence or autofluorescence in response to said incident femtosecond pulsed laser beam;
scanning the incident laser beam with an XY scanner to obtain two-dimensional image information of the ocular fundus; and
separating the generated fluorescence or autofluorescence with a dichroic mirror into at least a first wavelength range and a second wavelength range.

4. The fundus imaging method according to claim 3, wherein the fluorescence or autofluorescence is one of fluorescence generated from a fluorescent dye present in the ocular fundus to be examined and autofluorescence generated from a tissue of the ocular fundus to be examined.

5. An optical aberration correcting method, comprising:
adjusting a wavefront of a femtosecond pulsed laser beam from a laser light source that is incident on an ocular fundus to be examined so that an intensity of fluorescence or autofluorescence generated in a multi-photon excitation process by the femtosecond pulsed laser beam incident on the ocular fundus to be examined becomes a maximum value, at least a portion of the ocular fundus configured to generate said fluorescence or autofluorescence in response to said incident femtosecond pulsed laser beam;
scanning the incident laser beam with an XY scanner to obtain two-dimensional image information of the ocular fundus; and
separating the generated fluorescence or autofluorescence with a dichroic mirror into at least a first wavelength range and a second wavelength range.

6. The fundus imaging apparatus according to claim 1, further comprising a second detector, wherein the separated first wavelength range of the generated fluorescence or autofluorescence is output to the detector, and the separated second wavelength range of the generated fluorescence or autofluorescence is output to the second detector.

7. The fundus imaging apparatus according to claim 6, further comprising a display device configured to display a two-dimensional image of the ocular fundus based on the two-dimensional image information that is obtained by the XY scanner and that is separated by the dichroic mirror.

8. The optical aberration correcting apparatus according to claim 2, further comprising a second detector, wherein the separated first wavelength range of the generated fluorescence or autofluorescence is output to the detector, and the separated second wavelength range of the generated fluorescence or autofluorescence is output to the second detector.

9. The optical aberration correcting apparatus according to claim 8, further comprising a display device configured to display a two-dimensional image of the ocular fundus based on the two-dimensional image information that is obtained by the XY scanner and that is separated by the dichroic mirror.

10. The fundus imaging method according to claim 3, further comprising outputting the separated first wavelength range of the generated fluorescence or autofluorescence to the detector, and outputting the separated second wavelength range of the generated fluorescence or autofluorescence to a second detector.

11. The fundus imaging method according to claim 10, further comprising displaying a two-dimensional image of the ocular fundus based on the two-dimensional image information that is obtained by the XY scanner and that is separated by the dichroic mirror.

12. The optical aberration correcting method according to claim 5, further comprising outputting the separated first wavelength range of the generated fluorescence or autofluorescence to the detector, and outputting the separated second wavelength range of the generated fluorescence or autofluorescence to a second detector.

13. The optical aberration correcting method according to claim 12, further comprising displaying a two-dimensional image of the ocular fundus based on the two-dimensional image information that is obtained by the XY scanner and that is separated by the dichroic mirror.

* * * * *